US012580075B2

(12) United States Patent
Chen et al.

(10) Patent No.: US 12,580,075 B2
(45) Date of Patent: Mar. 17, 2026

(54) AUTOMATED CONVERSION OF DRUG LIBRARIES

(71) Applicant: CAREFUSION 303, INC., San Diego, CA (US)

(72) Inventors: Evan Chen, San Diego, CA (US); Claire Ellen Knight, Arlington, TX (US); Brian M. Sullivan, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 577 days.

(21) Appl. No.: 17/794,900

(22) PCT Filed: Jan. 13, 2021

(86) PCT No.: PCT/US2021/013305
§ 371 (c)(1),
(2) Date: Jul. 22, 2022

(87) PCT Pub. No.: WO2021/150408
PCT Pub. Date: Jul. 29, 2021

(65) Prior Publication Data
US 2023/0054746 A1 Feb. 23, 2023

Related U.S. Application Data

(60) Provisional application No. 62/965,107, filed on Jan. 23, 2020.

(51) Int. Cl.
*G16H 40/40* (2018.01)
*G06F 8/60* (2018.01)
*G16H 70/40* (2018.01)

(52) U.S. Cl.
CPC .............. *G16H 40/40* (2018.01); *G06F 8/60* (2013.01); *G16H 70/40* (2018.01)

(58) Field of Classification Search
CPC ........ G16H 40/40; G16H 70/40; G16H 40/67; G16H 40/63; G06F 8/60
See application file for complete search history.

(56) References Cited

U.S. PATENT DOCUMENTS 5,681,285 A 10/1997 Ford
5,713,856 A 2/1998 Eggers et al.
(Continued)

FOREIGN PATENT DOCUMENTS

WO WO-2019214929 A1 11/2019
WO WO-2019219290 A1 11/2019

OTHER PUBLICATIONS

International Preliminary Report on Patentability from the International Preliminary Examining Authority for Application No. PCT/US2021/013305, dated May 17, 2022, 28 pages.
(Continued)

*Primary Examiner* — David J Stoltenberg
*Assistant Examiner* — Tran N Nguyen
(74) *Attorney, Agent, or Firm* — MASCHOFF BRENNAN

(57) ABSTRACT

A system and method is disclosed for converting drug library packages. An existing drug library software package is automatically analyzed to determine existing drug library information compatible with a target library format corresponding to a target medical device type, and to identify drug library information omitted, missing, or needing editing from the existing drug library information. A user interface is provided for display to convert at least a portion of the identified drug library information to the second library format, and an instruction is received via the user interface to select one or more predetermined parameters in the target library format for assignment to a new drug library software package configured in the target library format based one or more corresponding parameters selected from (Continued)

the identified drug library information. The new drug library software package is generated based on the existing drug library information and the selected one or more predetermined parameters.

20 Claims, 5 Drawing Sheets

(56) References Cited

U.S. PATENT DOCUMENTS

| | | | |
|---|---|---|---|
| 7,539,684 B2 | 5/2009 | Gogolak et al. | |
| 11,309,070 B2 * | 4/2022 | Xavier ................. | A61M 5/172 |
| 11,901,070 B2 * | 2/2024 | Muhsin ............... | A61B 5/7445 |
| 2014/0180711 A1 * | 6/2014 | Kamen ................. | G16H 70/40 |
| | | | 705/2 |
| 2014/0278458 A1 * | 9/2014 | Borges .................. | G16H 40/60 |
| | | | 705/2 |
| 2016/0350513 A1 | 12/2016 | Jacobson et al. | |
| 2017/0043089 A1 * | 2/2017 | Handler ................ | H04L 67/56 |
| 2021/0233638 A1 * | 7/2021 | Moskal ................. | G16H 40/20 |

OTHER PUBLICATIONS

International Search Report and Written Opinion for Application No. PCT/US2021/013305, dated Apr. 16, 2021, 15 pages.
Written Opinion from the International Preliminary Examining Authority for Application No. PCT/US2021/013305, dated Feb. 1, 2022, 10 pages.
Australian Office Action for Application No. 2021209836, dated Dec. 12, 2022, 4 pages.

* cited by examiner

AUTOMATED CONVERSION OF DRUG LIBRARIES

TECHNICAL FIELD

This application relates generally to maintaining the operation of medical devices throughout a healthcare organization.

BACKGROUND

The process by which a patient care-giver takes to initiate drug delivery from an infusion pump or similar medical device is complex and if done incorrectly can lead to serious problems. The process is prone to error, especially because of the requirement for multiple computations and calculations. The complexities are aggravated by several factors. The staff training cost and the cost of preparing, updating, and distributing formularies and policy and procedure protocols within hospitals is large. The difficulty of establishing safe and uniform practices is compounded by significant local, regional, and nation-to-nation variations in practice patterns. The complexity of using such pumps may result in denial of needed therapy to patients because a care-giver lacks sufficient training, or does not have ready access or the time to review relevant knowledge or to use other tools (such as computational devices) to effect the process of delivering a needed medication infusion to a specific patient.

Various technological approaches have been taken in the past to make infusion pumps more suitable for intravenous drug infusions. For example, companies have developed calculator-type infusion pumps which allow users to deliver drug diluted in a fluid by entering data such as drug concentration, patient weight, and desired doses and dose rates using dose delivery units such as mcg/kg or mcg/kg/min. Based upon these inputs, the pumps calculate the volumes and fluid flow rates to be delivered.

Approaches to making fluid infusion pumps more suitable for drug infusion have included the development of pumps which contain microprocessor controllers and EPROM devices containing preprogrammed information including a series of drug infusion profiles relating to various drugs to be infused. These drug libraries can be downloaded to and which electronically modify (i.e., program) the infusion pump. These libraries may include, for example, drug-, drug-concentration-, drug-container-size-, bolus-rate-, and dose-delivery-unit-specific parameters. The parameters may identify, for example, minimum values, maximum values, or specific ranges for a programmable infusion parameter. In addition, if a particular drug delivery configuration will be used simultaneously on multiple pumps within a facility, a copy may be downloaded for each pump.

These libraries, however, are often manufacturer-specific and thus a different type of library may be required for each pump type. If a hospital wishes to implement a different type of pump then a new drug library must typically be created, as the currently used drug library will often be found to be incompatible.

SUMMARY

According to various aspects, the subject technology includes a system and method for converting a drug library specific to one medical system to a format compatible with another medical system. A first existing drug library software package is automatically analyzed to determine first existing drug library information compatible with a second target library format corresponding to a second target medical device type, and to determine drug library information omitted, missing, or needing editing from the existing compatible drug library information. A user interface is provided for display to convert at least a portion of the drug library information not within the compatible drug library information to the second library format, and an instruction is received via the user interface to select one or more predetermined parameters in the target library format for assignment to a new drug library software package configured in the target library format based on one or more corresponding parameters selected from the drug library information identified as not being within the compatible drug library information. The new drug library software package is generated based on the existing drug library information and the selected one or more predetermined parameters.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

The subject technology includes a system and method for converting a drug library specific to one medical system to a format compatible with another medical system. An existing drug library software package is imported into the system or otherwise identified, and then automatically analyzed to determine existing drug library information compatible with a target library format corresponding to a target medical device type. Second drug library information not immediately compatible with the target library format is identified, and user interface is provided for display to convert at least a portion of the second (e.g., not compatible) drug library information to the target library format. An instruction is received via the user interface to select one or more predetermined parameters in the target library format for assignment to a new drug library software package configured in the target library format based one or more corresponding parameters selected from the second drug library information. The new drug library software package is generated based on the compatible drug library information and the selected one or more predetermined parameters.

Figure 1A:
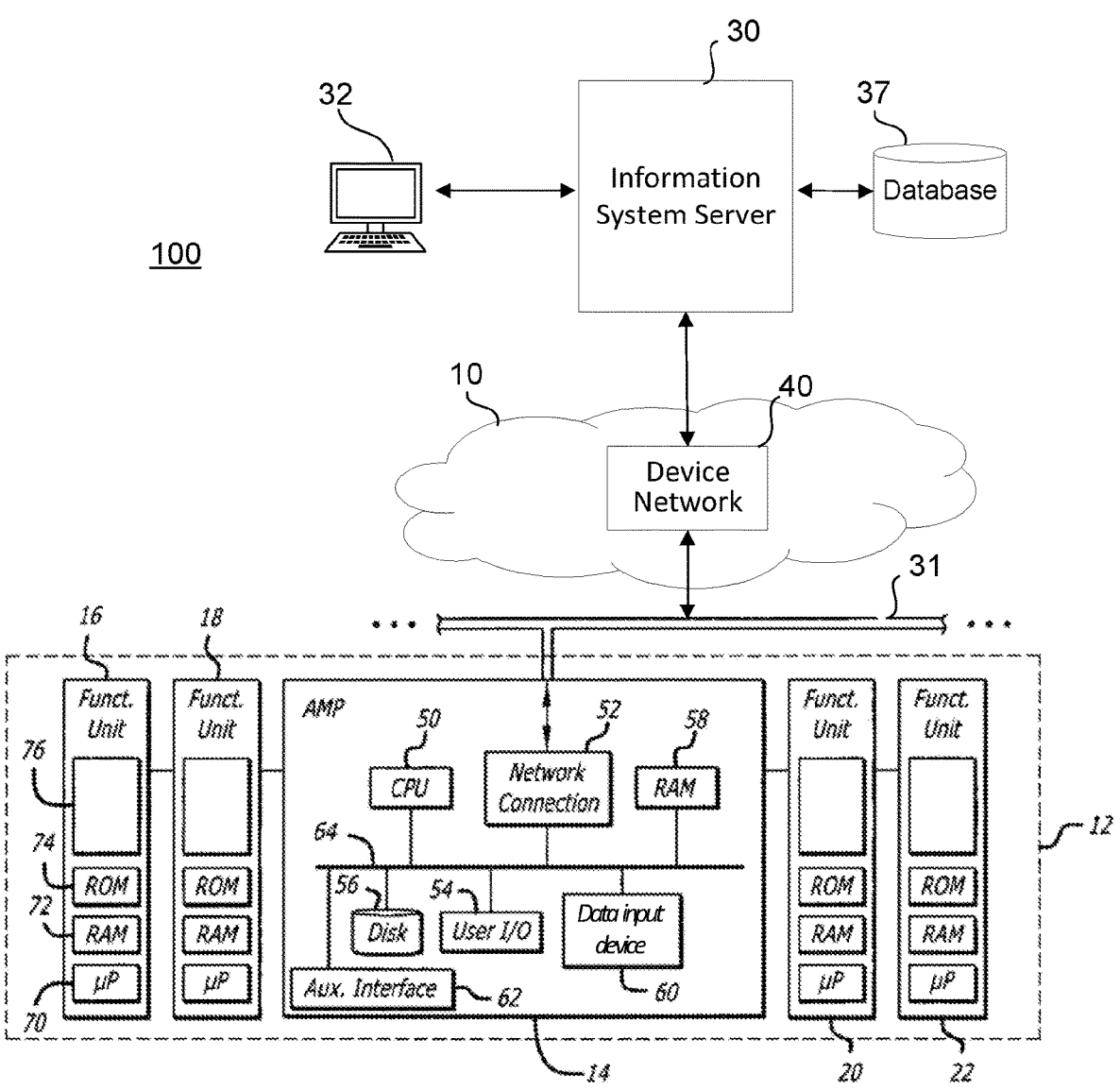
FIG. 1A depicts an example of an institutional patient care system of a healthcare organization, according to aspects of the subject technology.

FIG. 1A depicts an example of an institutional patient care system 100 of a healthcare organization, according to aspects of the subject technology. In FIG. 1A, a patient care device (or "medical device" generally) 12 is connected to a hospital network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which patient care devices 12 (and other devices) communicate in accordance with normal operations.

Additionally, institutional patient care system 100 may incorporate a separate information system server 30, the function of which will be described in more detail below. Moreover, although the information system server 30 is shown as a separate server, the functions and programming of the information system server 30 may be incorporated into another computer, if such is desired by engineers designing the institution's information system. Institutional patient care system 100 may further include one or multiple device terminals 32 for connecting and communicating with information system server 30. Device terminals 32 may include personal computers, personal data assistances, mobile devices such as laptops, tablet computers, augmented reality devices, or smartphones, configured with software for communications with information system server 30 via network 10.

Patient care device 12 comprises a system for providing patient care, such as that described in U.S. Pat. No. 5,713, 856 to Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54 (e.g., a display screen and/or keyboard), a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 16.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. Each mode or personality may include a different set of configuration parameters, or implement a different drug library, as described below. The configuration database may be a database 56 internal to patient care device, or an external database 37. A particular configuration database (or portion thereof) may be selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

A controller 14 of patient care device 12 also has access to a drug library. Further information on drug libraries is contained in U.S. Pat. No. 5,681,285 to Ford, which is incorporated herein by reference in its entirety. The drug library may be resident in the controller, in a local accessible memory, or may be located elsewhere on the system network but be accessible by the controller. A drug library may include one or more drug entries, with each entry being associated with a set of drug delivery parameters and/or protocols for configuring a programmable infusion device when the drug library, including its parameters and/or protocols, is loaded into a memory of the programmable infusion device. If data is missing from the drug library or is out of range for the infusion device or is otherwise not allowed by the infusion device then the infusion device may issue an error response.

"Drug Library Profiles" may be established in which medications (e.g., drugs), concentrations, and other pumping parameters are set particular to that care area-such as, for example, an ICU (intensive care unit) profile, a pediatric profile, a neonatal profile and others. Data sets of medications allowed for use and configurations of pumping parameters including limitations for that use may be available for each drug library profile. As such, drug library profiles may, although not necessarily, correspond to different patient care areas of the hospital. Thus a controller 14 located in a pediatric ward, for example, may utilize a pediatric drug library profile that includes sets of allowed medications, pumping parameters, and pumping limitations that are specific to patients classified as pediatric or located in a pediatric ward. Similarly, a controller 14 located in an ICU may utilize an ICU drug library profile that includes a different set of allowed medications, pumping parameters, and pumping limitations that are specific to patients located in an intensive care environment and other patients requiring intensive care.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

Figure 1B:
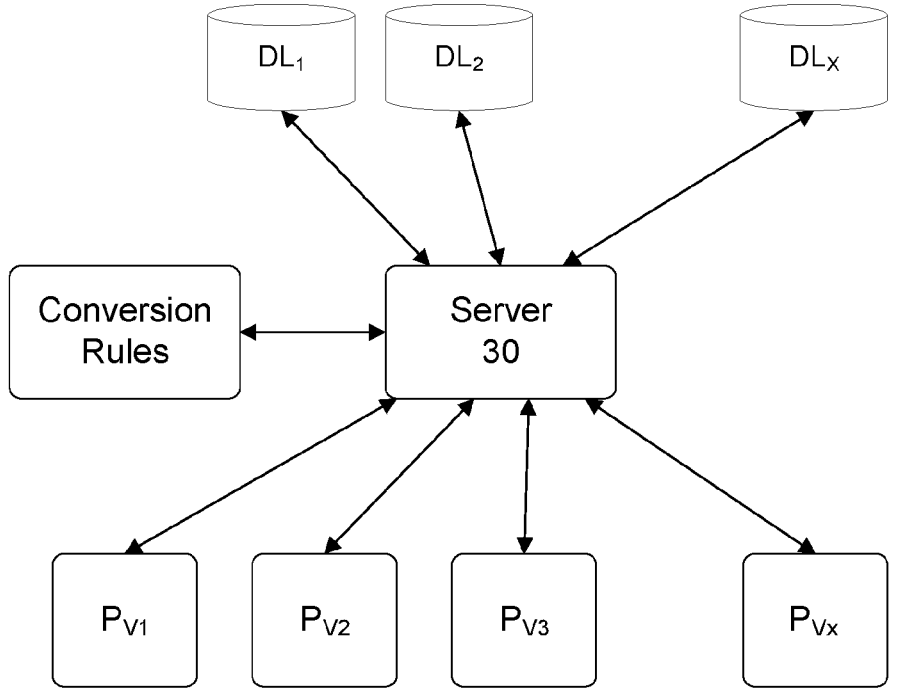
FIG. 1B depicts an example server system for converting drug libraries between various formats using conversion rules, according to aspects of the subject technology.

FIG. 1B depicts an example server system for converting drug libraries between various formats using conversion rules, according to aspects of the subject technology. One or more physically or logically separated databases (e.g., database 37 in FIG. 1A) may store multiple drug libraries $DL_1$-$DL_X$. According to various aspects, each drug library may be associated with one or more medical devices $P_{V1}$-$P_{Vx}$ which may include the patient care device 21 shown in FIG. 1A. Server 30 may access a set of conversion rules for converting a drug library specific to one type of medical device to another type of medical device, particularly wherein the different types of medical devices use different data formats or parameters. For example, a first drug library may be specific to a first infusion pump, and a second drug library may be specific to a second infusion pump, while a third pump may not be associated with any drug library. The conversion rules may store information for converting certain parameters and/or values to a format compatible with the third pump. The system may utilize the conversion rules to identify and convert a particular preexisting drug library (e.g., $DL_1$) to a drug library compatible with the third pump. One reason the third pump may need the conversion is because the third pump may not require a drug library but be configured to operate according to data sets for configuring pumping parameters. In this example, the system may obtain a data set which contains drug medication and pumping parameters from the preexisting drug library and convert the obtained information to the pumping parameters (not necessarily a full drug library entry) into a machine readable format that can be used by the third pump. Another reason the third pump may need the conversion is because the drug library supporting the third pump does not include an entry or includes a deficient entry. In such instances, the system may convert both the drug library from a first format to a second format understandable by the third pump as well as the pumping parameters from the first format to a second format understandable by the third pump. The conversion rules may be updated from time to time by user input (e.g., via a user interface), or automatically based on machine learning or other artificial intelligence algorithms.

One or more aspects of the artificial intelligence described may be implemented in whole or in part by a model. A model may be implemented as a machine learning model. The learning may be supervised, unsupervised, reinforced, or a hybrid learning whereby multiple learning techniques are employed to generate the model. The learning may be performed as part of training. Training the model may include obtaining a set of training data and adjusting characteristics of the model to obtain a desired model output. For example, three characteristics may be associated with a desired device state. In such instance, the training may include receiving the three characteristics as inputs to the model and adjusting the characteristics of the model such that for each set of three characteristics, the output device state matches the desired device state associated with the historical data.

In some implementations, the training may be dynamic. For example, the system may update the model using a set of events. The detectable properties from the events may be used to adjust the model.

The model may be an equation, artificial neural network, recurrent neural network, convolutional neural network, decision tree, or other machine readable artificial intelligence structure. The characteristics of the structure available for adjusting during training may vary based on the model selected. For example, if a neural network is the selected model, characteristics may include input elements, network layers, node density, node activation thresholds, weights between nodes, input or output value weights, or the like. If the model is implemented as an equation (e.g., regression), the characteristics may include weights for the input parameters, thresholds or limits for evaluating an output value, or criterion for selecting from a set of equations.

Once a model is trained, retraining may be included to refine or update the model to reflect additional data or specific operational conditions. The retraining may be based on one or more signals detected by a device described herein or as part of a method described herein. Upon detection of the designated signals, the system may activate a training process to adjust the model as described.

Further examples of machine learning and modeling features which may be included in the embodiments discussed above are described in "A survey of machine learning for big data processing" by Qiu et al. in EURASIP Journal on Advances in Signal Processing (2016) which is hereby incorporated by reference in its entirety.

Figure 2:
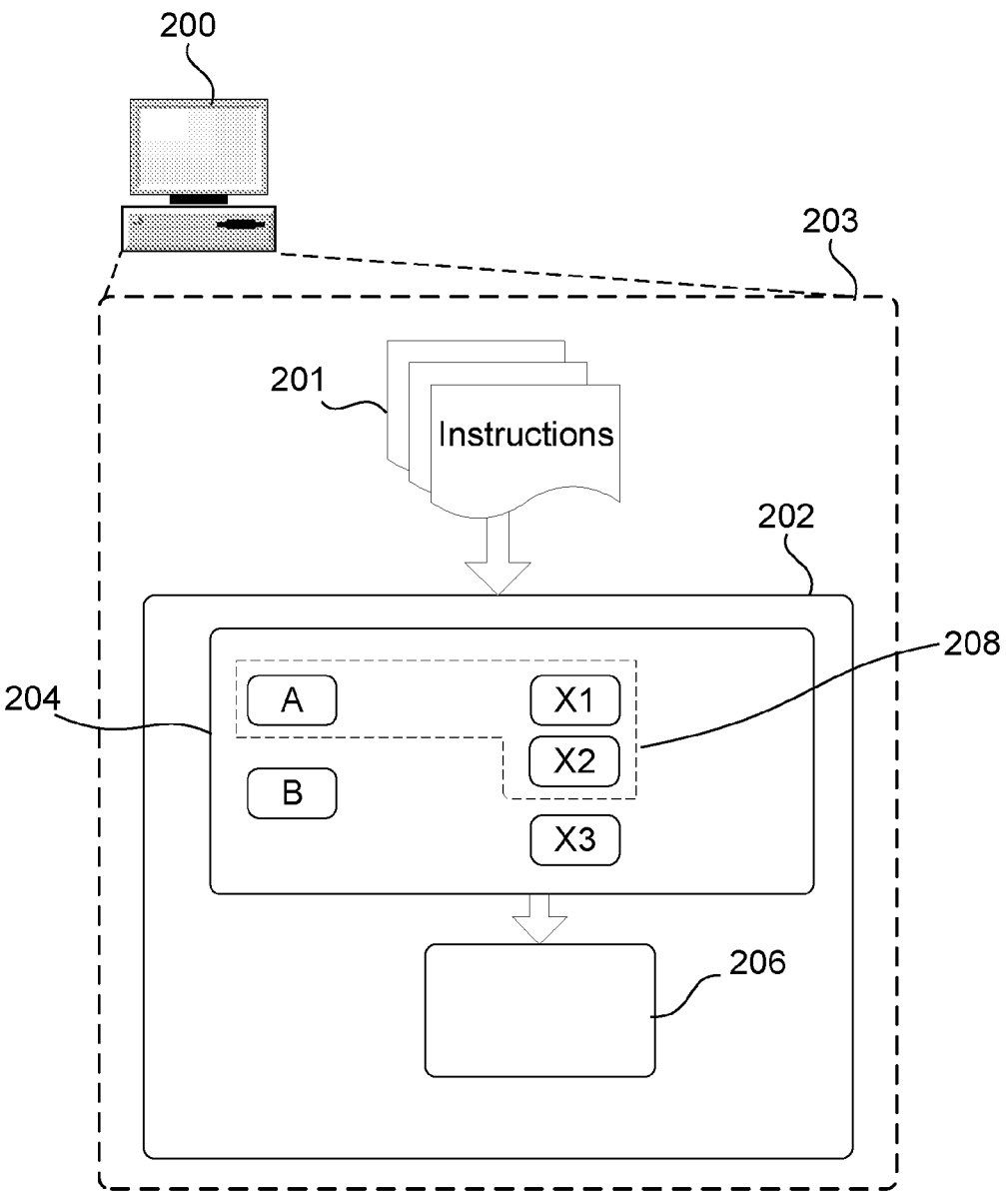
FIG. 2 depicts an example system, including a computing device and user interface for importing and translating drug libraries from various vendor platforms into a standardized format for use on a specified platform, in accordance with aspects of the subject technology.

FIG. 2 depicts an example system, including a computing device 200 and user interface 202 for importing and translating drug libraries from various vendor platforms into a standardized format for use on a specified platform, in accordance with aspects of the subject technology. During operation of a computing device 200, executable instructions 201 are loaded into a runtime environment 203 and executed. Instructions 201, when executed, create user interface 202, and/or a second designer user interface 204, and may perform a number of operations upon data provided for display in user interfaces 202 and 204. According to various aspects, computing device 200 may be implemented as information system server 30, and user interface 202 and/or designer user interface 204 may be transmitted over a network to computing device 32 remote from server 30 for display on a display screen associated with computing device 32, to medical device 12 for display on a display screen of controller 14, or other display screen.

As depicted in the example of FIG. 2, user interface 202 may include, for example, a designer interface 204 (or software "wizard"), which may include selectable and/or updatable data fields, that enables a user to visually build (e.g., using controls) a drug library 206 using predetermined conversion rules, in connection with various console inputs and/or drag-and-drop operations. During creation by a user using the designer interface 204, the drug library to be generated may be visually represented at runtime by multiple field layouts 208, each with a different arrangement of data elements for a medical device format. As will be described further, instructions 201 which render the user interface 202 may be stored on a server 30, and accessed by a browser or other local application on a computing device 32 remote from the server. For example, the user interface may be presented to a medical device 12 for display on a display screen of controller 14.

Computer program code for carrying out operations of the subject technology may be written in an object oriented programming language such as, for example, JAVA®, Smalltalk, or C++. However, the computer program code for carrying out operations of the subject technology may also be written in conventional procedural programming languages, such as the "C" programming language, in an interpreted scripting language, such as Perl, or in a functional (or fourth generation) programming language such as Lisp, SML, Forth, or the like. The software may also be written to be compatible with HLA-7 requirements.

Computing device 200 may be a stand-alone device, or a server computing device 30, remotely positioned from a client computing device 32 wherein user interface 202 is displayed. In client-server implementations, the client computing device 32, and the application which renders user interface 202 may also be represented by FIG. 2. For example, instructions 108 may be implemented by a network-enabled application, which retrieves user interface 108 from the server and displays the application to the user.

In some implementations, the creation process may store rules for converting information stored in the existing drug library rather than generating a new, converted, drug library. The rules may be associated with one or more selection criteria to identify target platforms for using a specific rule. The selection criteria may include a pump vendor identifier, drug library vendor identifier, pump firmware identifier, version information, or other detectable characteristic of the medical device. A medical device may be configured to query a server (e.g., server 30) to obtain drug library information. The server may then identify a drug library (e.g., one or more of $DL_1$ through $DL_x$) that includes the drug library information for the drug to be delivered. The identification may be based on a message received from the medical device identifying (directly or indirectly) the drug.

Once identified, the server may determine whether the drug library information is in a format that is understood by the requesting medical device. The determination may be based on information received from the drug library such as vendor identification information, version information, or the like. The determination may additionally or alternatively be based on information stored in a data storage accessible by the server. One examples of such information is a compatibility matrix correlating medical devices and drug libraries. If the library is deemed compatible, the server may transmit a message including the drug library information to the requesting medical device. If the library is deemed incompatible, the server may then identify one or more conversion rules to translate the drug library information into a format that can be used by the requesting medical device. The identification of a conversion rule may be based on one or more of: a characteristic of the medical device, a characteristic of the drug library from which the drug library information was retrieved, information included in the request message received from the medical device (e.g., drug to be delivered), or the like. Once identified, the server may use the conversion rule to generate a message including the drug library information in a format that can be used by the requesting medical device.

In some instances, the drug libraries and/or conversion rules may not be established for a request from a medical device. In such instances, the medical device may present a perceivable indication that the drug cannot be delivered using a drug library. Some medical devices will offer an alternate mode of operation to proceed with the delivery but without the safety measures offered by the drug library information. Such instances may also generate a perceivable indication to a manager of the drug library identifying the missing information that was needed to fulfill the request. This indication may be presented via a user interface and initiate a workflow to generate the appropriate library entries and/or conversion rule(s).

Figure 3:
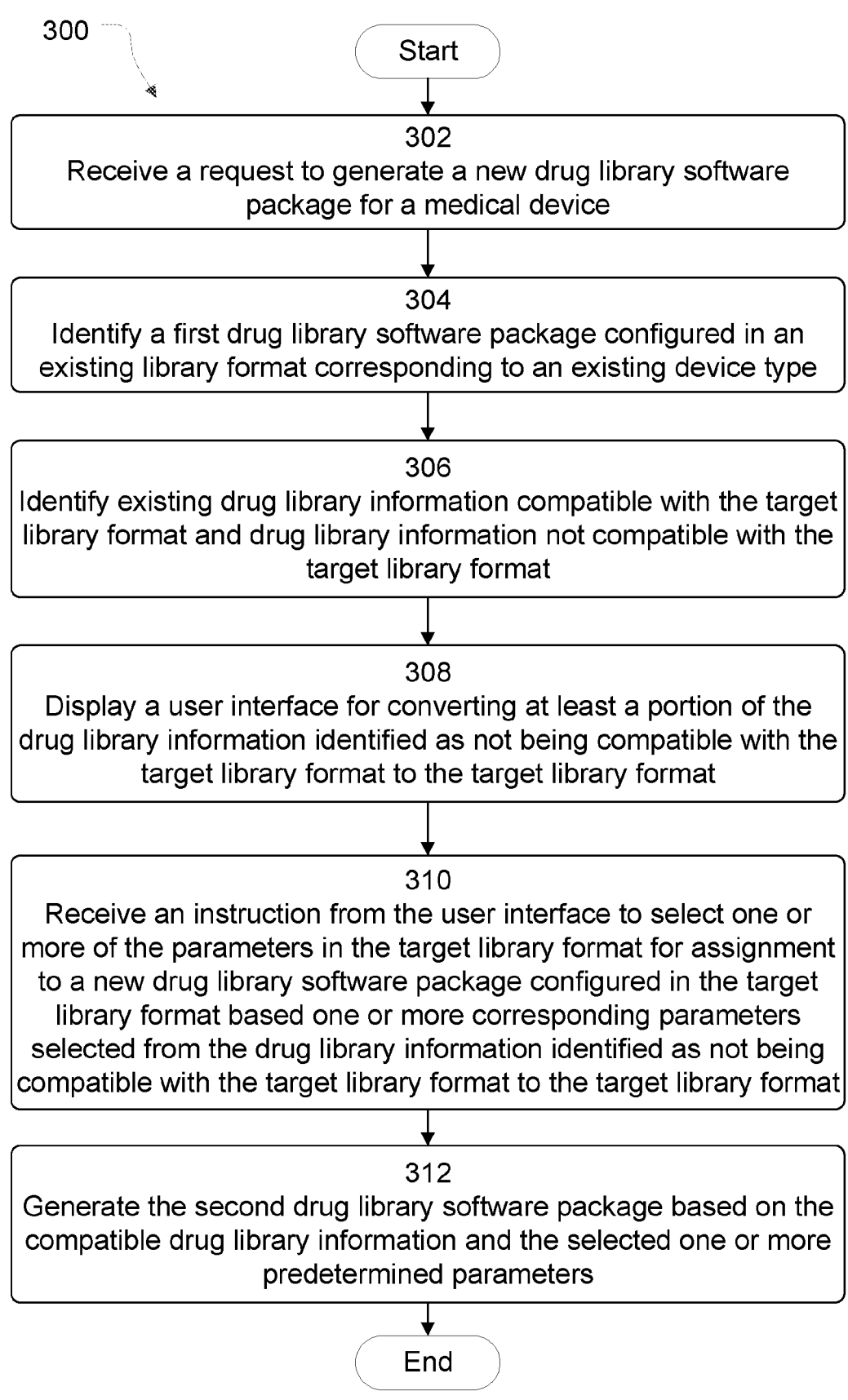
FIG. 3 depicts an example process for importing and translating drug libraries from various vendor platforms into a standardized format for use on a specified platform, according to aspects of the subject technology.

FIG. 3 depicts an example process for importing and translating drug libraries from various vendor platforms into a standardized format for use on a specified platform, according to aspects of the subject technology. For explanatory purposes, the various blocks of example process 300 are described herein with reference to FIGS. 1A, 1B, and 2, and the components and/or processes described herein. The one or more of the blocks of process 300 may be implemented, for example, by one or more computing devices including, for example, medical device 12. In some implementations, one or more of the blocks may be implemented apart from other blocks, and by one or more different processors or devices. Further for explanatory purposes, the blocks of example process 300 are described as occurring in serial, or linearly. However, multiple blocks of example process 300 may occur in parallel. In addition, the blocks of example process 300 need not be performed in the order shown and/or one or more of the blocks of example process 300 need not be performed.

In the depicted example, a request to generate a new drug library software package for a medical device 14 is received (302). The request may be received, for example, at a server 30 from a first user interface 202. In some implementations, the first user interface 202 may be displayed on a client computer 32 connected to network 10. Additionally or in the alternative, first user interface 202 may be displayed on a display device 54 of a medical device 14. It is understood that the actions described herein as being performed by a server or client computer may be performed or orchestrated by a local computing device or terminal 32, or by a medical device 12 having a similarly situated processor 50.

According to various aspects, the foregoing request may represent or include a request to generate a drug library software package 206 for use by a new type of medical device 14 within the healthcare organization. The request may include generating the new drug library software package 206 based on an existing drug library (not shown) used by a type of medical device 14 currently deployed within the healthcare organization. In this regard, the received request may include a selection of a first existing drug library software package that includes certain operating parameters or configuration information currently in use by a type of medical device 14 deployed within the healthcare organization. Accordingly, the request may include first identifier associated with the first existing drug library, which may identify the first existing drug library (or a set of corresponding information) in a database 37. The request may also include a second identifier that may be used to identify a target (e.g., new), second type of medical device 14 that will be used in the medical organization. In some implementations, the first existing drug library may be imported into the system (e.g., using interface 202), together with metadata describing the library. While the term "software package" generally describes software that may be implemented on a computing device, the terms "drug library" and "drug library software package" may be used herein synonymously to describe drug library information usable to configure and/or operate a medical device 14.

Upon identification, the server 30 identifies the first existing drug library software package as being configured in a first existing library format corresponding to a first existing medical device type (304). In this regard, database 37 may store metadata for each library used by the system, including type of library, types of parameters, value ranges, etc. Similar metadata may be input (e.g., via user interface 202) and/or stored in database 37 for the target (e.g., new), second type of medical device. The server 30 performs a lookup to determine the format corresponding to the device type based on the received identifier. The system also stores predetermined conversion rules (FIG. 1B) which may be specific to converting data from one drug library to another.

The second target type of medical device 14 may utilize drug library software packages that are, or include information, configured in a second target library format that is not compatible with the first existing library format. On receiving the identifications of the first existing device type and the second target device type, computing device 200 automatically analyzes, based on the conversion rules, the first existing drug library software package to identify existing drug library information compatible with the target library format, and identify drug library information not within the compatible drug library information (306) (e.g., library information that is omitted or missing from the compatible information, or in need of editing to be compatible). In this regard, computing device 200 determines first existing drug library information compatible with the second target library format corresponding to the second target medical device type. Not all data fields utilized by one library type will have a corresponding data field accurately represented in the other library type. Data in fields identified by corresponding metadata as being compatible are transferred. As part of this process, computing device 200 may automatically identify drug library information not within the existing drug library information compatible with the target library format, for example, as a consequence of not being able to determine a compatibility between the data fields.

A second designer user interface 204 is provided for display for converting at least a portion of the drug library information identified as not being compatible with the target library format to the second target library format (308). The designer interface 204 may operate with or implement a computer learning algorithm or other program that automatically determines, in connection with the conversion rules and/or user input, which parameters of the identified omitted drug library information can be converted to the second target library format, and initiate performing such conversion for the user. In this regard, computing device 200 may automatically implement a mapping filter that may populate fields automatically. The designer interface 204 may then present a list of parameters that were automatically converted for verification by the user, while presenting a list of parameters that were not automatically converted to the second target library format in the prior step.

The computing device 200 may receive an indication that the one or more corresponding parameters were selected and determine, responsive to receiving the indication, an equivalent one of the one or more predetermined parameters for each of the selected one or more corresponding parameters. Computing device 200 may, within the designer user interface 204, present the equivalent parameters as replacement parameters for selection by a user. For example, computing device 200 may determine that a first parameter or parameter type of the first existing library format is within a range of values corresponding to one or more respective parameters or parameter types of the second target library format. Computing device 200 selects the one or more respective parameters based on a likelihood that the parameters are a fit for the data. The parameters or parameter types may then be presented via the designer interface 204 for selection and/or confirmation. For example, as depicted in the example of FIG. 2, computing device 200 may determine that the second target device format includes three different possible values (or ranges) X1, X2, and X3 for a certain parameter. At the same time, computing device 200 may determine that a possible corresponding parameter A in the first existing device format may fit into either X1 or X2. The designer interface 204 may then present parameters X1 and X2 as options for replacement of parameter A to the user.

An instruction is received (e.g., by server 30) from user interface 202, 204 to select one or more of the parameters in the second target library format for assignment to the new drug library software package configured in the second target library format based one or more corresponding parameters selected from the drug library information not within the compatible drug library information (310). For example, the user may select X2 as corresponding to parameter A of the first existing drug library format. The user may also select some or all of the listed parameters for deletion. For example, the user may determine that parameter B is no longer used by the second target drug library format (or the second type of medical device 14), and omit parameter B or any corresponding parameter from inclusion in the new drug library package. According to some implementations, the instruction to select one or more predetermined parameters may operate as a confirmation that the one or more predetermined parameters are the most equivalent parameters to the one or more corresponding parameters.

When all of the parameters have been accounted for, or upon indication from the user (via designer interface 204), the computing device 200 generates the new drug library software package based on the existing drug library information and the selected one or more predetermined parameters (312). According to various implementations, the new drug library software package 206 may then be provided to a medical device of the target medical device type. The drug library software package may be manually loaded into the medical device 14, or downloaded automatically via device network 40 and transmission channel 31.

Many of the above-described example 300, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 4:
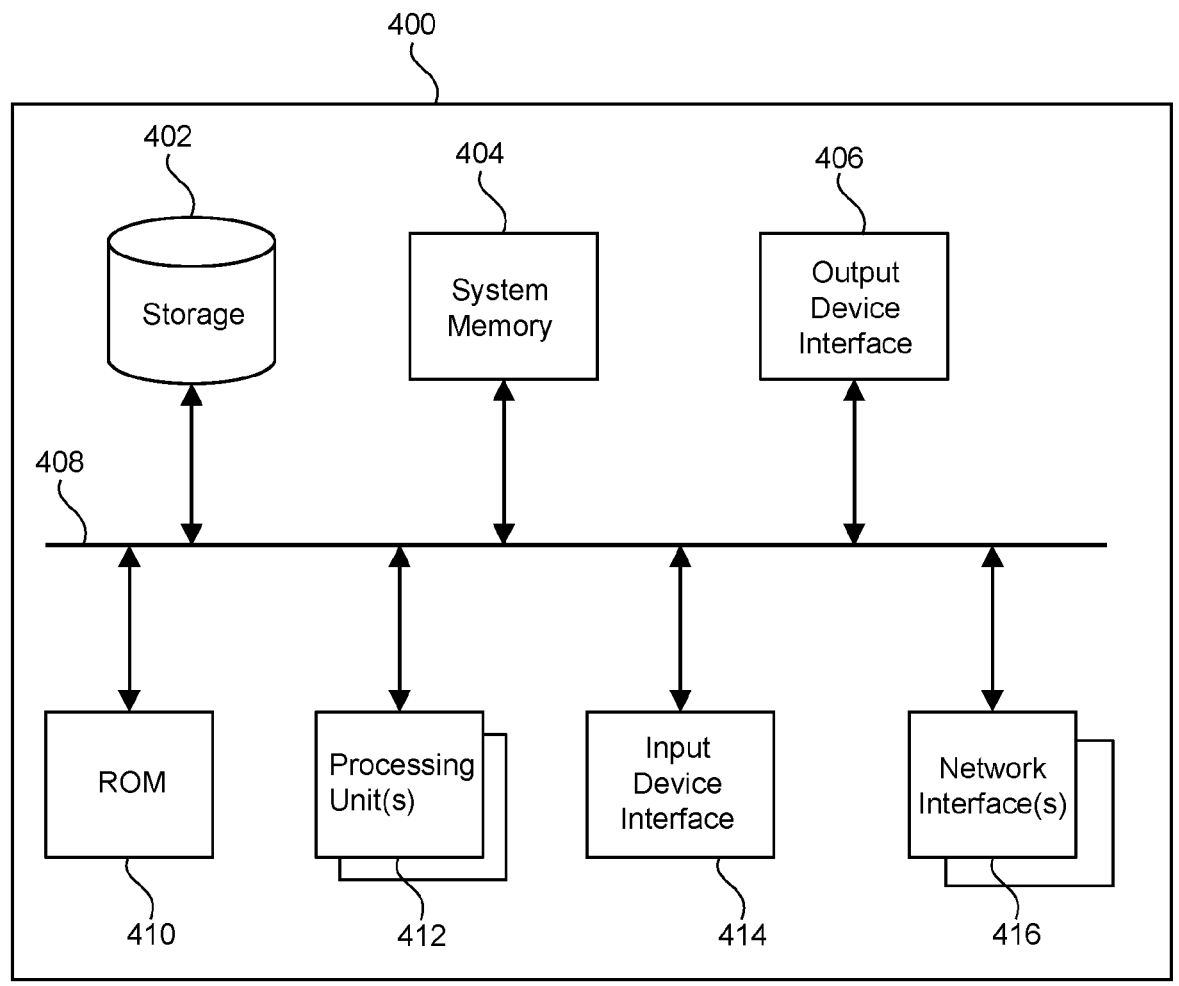
FIG. 4 is a conceptual diagram illustrating an example electronic system for importing and translating drug libraries from various vendor platforms into a standardized format for use on a specified platform, according to aspects of the subject technology.

FIG. 4 is a conceptual diagram illustrating an example electronic system 400 for importing and translating drug libraries from various vendor platforms into a standardized format for use on a specified platform, according to aspects of the subject technology. Electronic system 400 may be a computing device for execution of software associated with one or more portions or steps of process 400, or components and processes provided by FIGS. 1-3, including but not limited to information system server 30, production server 204, computing hardware within patient care device 12, or terminal device 37. Electronic system 400 may be representative, in combination with the disclosure regarding FIGS. 1-3. In this regard, electronic system 400 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 400 may include various types of computer readable media and interfaces for various other types of computer readable media. In the depicted example, electronic system 400 includes a bus 408, processing unit(s) 412, a system memory 404, a read-only memory (ROM) 410, a permanent storage device 402, an input device interface 614, an output device interface 406, and one or more network interfaces 416. In some implementations, electronic system 400 may include or be integrated with other computing devices or circuitry for operation of the various components and processes previously described.

Bus 408 collectively represents all system, peripheral, and chipset buses that communicatively connect the numerous internal devices of electronic system 400. For instance, bus 408 communicatively connects processing unit(s) 412 with ROM 410, system memory 404, and permanent storage device 402.

From these various memory units, processing unit(s) 412 retrieves instructions to execute and data to process in order to execute the processes of the subject disclosure. The processing unit(s) can be a single processor or a multi-core processor in different implementations.

ROM 410 stores static data and instructions that are needed by processing unit(s) 412 and other modules of the electronic system. Permanent storage device 402, on the other hand, is a read-and-write memory device. This device is a non-volatile memory unit that stores instructions and data even when electronic system 400 is off. Some implementations of the subject disclosure use a mass-storage device (such as a magnetic or optical disk and its corresponding disk drive) as permanent storage device 402.

Other implementations use a removable storage device (such as a floppy disk, flash drive, and its corresponding disk drive) as permanent storage device 402. Like permanent storage device 402, system memory 404 is a read-and-write memory device. However, unlike storage device 402, system memory 404 is a volatile read-and-write memory, such a random access memory. System memory 404 stores some of the instructions and data that the processor needs at runtime. In some implementations, the processes of the subject disclosure are stored in system memory 404, permanent storage device 402, and/or ROM 410. From these various memory units, processing unit(s) 412 retrieves instructions to execute and data to process in order to execute the processes of some implementations.

Bus 408 also connects to input and output device interfaces 414 and 406. Input device interface 414 enables the user to communicate information and select commands to the electronic system. Input devices used with input device interface 414 include, e.g., alphanumeric keyboards and pointing devices (also called "cursor control devices"). Output device interfaces 406 enables, e.g., the display of images generated by the electronic system 400. Output devices used with output device interface 406 include, e.g., printers and display devices, such as cathode ray tubes (CRT) or liquid crystal displays (LCD). Some implementations include devices such as a touchscreen that functions as both input and output devices.

Also, as shown in FIG. 4, bus 408 also couples electronic system 400 to a network (not shown) through network interfaces 416. Network interfaces 416 may include, e.g., a wireless access point (e.g., Bluetooth or WiFi) or radio circuitry for connecting to a wireless access point. Network interfaces 416 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 400 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses:

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method, comprising: identifying an existing drug library software package configured in an existing library format corresponding to an existing medical device type; automatically analyzing the existing drug library software package to determine existing drug library information compatible with a target library format corresponding to a target medical device type, and to identify drug library information not within the existing compatible drug library information; providing for display a user interface for converting at least a portion of the drug library information identified as not being within the compatible drug library information to the target library format; receiving, via the user interface, an instruction to select one or more predetermined parameters in the target library format for assignment to a new drug library software package configured in the target library format based on one or more corresponding parameters selected from the drug library information identified as not being within the compatible drug library information; and generating the new drug library software package in the target library format based on the compatible drug library information and the selected one or more predetermined parameters.

Clause 2. The method of Clause 1, further comprising: receiving, at a server, a request to generate the new drug library software package for a medical device, and a selection of the existing drug library software package, wherein the existing drug library software package is identified in a database by the server responsive to receiving the request and selection, and wherein the analyzing, providing of the user interface, receiving, and generating are performed by the server.

Clause 3. The method of Clause 2, further comprising: providing the new drug library software package to the medical device of the target medical device type.

Clause 4. The method of Clause 1, further comprising: receiving, via the user interface, an indication that the one or more corresponding parameters were selected; determining, responsive to receiving the indication, an equivalent one of the one or more predetermined parameters for each of the selected one or more corresponding parameters; and presenting the equivalent parameters as replacement parameters, wherein the instruction to select one or more predetermined parameters comprises a confirmation that the one or more predetermined parameters are most equivalent parameters to the one or more corresponding parameters.

Clause 5. The method of Clause 4, wherein determining the equivalent one of the one or more predetermined parameters comprises: determining, for a first parameter of the one or more corresponding parameters, that the first parameter is within a range of values corresponding to a respective parameter of the predetermined parameters.

Clause 6. The method of Clause 1, receiving, via the user interface, an instruction to delete a parameter of the drug library information identified as not being within the compatible drug library information.

Clause 7. The method of Clause 1, further comprising: receiving, at a server, from a medical device a first indication of the medical device and a second indication of the existing drug library software package for operation on the medical device; determining, based on receiving the first indication and the second indication, that the medical device is of the target medical device type, and that the existing drug library software package is associated with the existing medical device type and incompatible with the target medical device type; and responsive to determining that the existing drug library software package is associated with the existing medical device type and the medical device is of the target medical device type, performing the identifying, analyzing steps, and providing steps.

Clause 8. A system, comprising one or more processors; and memory including instructions that, when executed by the one or more processors, cause the one or more processors to: identify an existing drug library software package configured in an existing library format corresponding to an existing medical device type; automatically analyze the existing drug library software package to determine existing drug library information compatible with a target library format corresponding to a target medical device type, and to identify drug library information not within the existing drug library information compatible with the target library format; provide for display a user interface for converting at least a portion of the drug library information identified as not being within the compatible drug library information to the target library format; receive, via the user interface, an instruction to select one or more predetermined parameters in the target library format for assignment to a new drug library software package configured in the target library format based on one or more corresponding parameters selected from the drug library information identified as not being within the compatible drug library information; and generate the new drug library software package in the target library format based on the compatible drug library information and the selected one or more predetermined parameters.

Clause 9. The system of Clause 8, wherein the instructions, when executed, further cause the one or more processors to: receive, at a server, a request to generate the new drug library software package for a medical device of the target medical device type, and a selection of the existing drug library software package, wherein the existing drug library software package is identified in a database by the server responsive to receiving the request and selection, and wherein the analyzing, providing of the user interface, receiving, and generating are performed over a network.

Clause 10. The system of Clause 9, wherein the instructions, when executed, further cause the one or more processors to: provide the new drug library software package to the medical device of the target medical device type.

Clause 11. The system of Clause 8, wherein the instructions, when executed, further cause the one or more processors to: receive, via the user interface, an indication that the one or more corresponding parameters were selected; determine, responsive to receiving the indication, an equivalent one of the one or more predetermined parameters for each of the selected one or more corresponding parameters; and provide the equivalent parameters as replacement parameters, wherein the instruction to select one or more predetermined parameters comprises a confirmation that the one or more predetermined parameters are most equivalent parameters to the one or more corresponding parameters.

Clause 12. The system of Clause 11, wherein determining the equivalent one of the one or more predetermined parameters comprises: causing the one or more processors to determine, for a first parameter of the one or more corresponding parameters, that the first parameter is within a range of values corresponding to a respective parameter of the predetermined parameters.

Clause 13. The system of Clause 8, wherein the instructions, when executed, further cause the one or more processors to: receive, via the user interface, an instruction to delete a parameter of the drug library information identified as not being within the compatible drug library information.

Clause 14. The system of Clause 8, wherein the instructions, when executed, further cause the one or more processors to: receiving, at a server, a first indication of a medical device and a second indication of the existing drug library software package for operation on the medical device; determining, based on receiving the first indication and the second indication, that the medical device is of the target medical device type, and that the existing drug library software package is associated with the existing medical device type and incompatible with the target medical device type; and responsive to determining that the existing drug library software package is associated with the existing medical device type and the medical device is of the target medical device type, performing the identifying, analyzing steps, and providing steps.

Clause 15. The system of Clause 14, wherein the user interface is provided for display at the medical device.

Clause 16. A non-transitory machine-readable storage medium embodying instructions that, when executed by a machine, cause the machine to perform operations comprising: identifying an existing drug library software package configured in an existing library format corresponding to an existing medical device type; automatically analyzing the existing drug library software package to determine existing drug library information compatible with a target library format corresponding to a target medical device type, and to identify drug library information not within the existing drug library information compatible with the target library format; providing for display a user interface for converting at least a portion of the drug library information identified as not being within the compatible drug library information to the target library format; receiving, via the user interface, an instruction to select one or more predetermined parameters in the target library format for assignment to a new drug library software package configured in the target library format based on one or more corresponding parameters selected from the drug library information identified as not being within the compatible drug library information; and generating the new drug library software package in the target library format based on the compatible drug library information and the selected one or more predetermined parameters.

Clause 17. The non-transitory machine-readable storage medium of Clause 16, wherein the operations further comprise: receiving, at a server, a request to generate the new drug library software package for a medical device of new second medical device type, and a selection of the existing drug library software package, wherein the existing drug library software package is identified in a database by the server responsive to receiving the request and selection, and wherein the analyzing, providing of the user interface, receiving, and generating are performed by the server.

Clause 18. The non-transitory machine-readable storage medium of Clause 17, wherein the operations further comprise: providing the new drug library software package to the medical device of the second medical device type.

Clause 19. The non-transitory machine-readable storage medium of Clause 16, further comprising: receiving, via the user interface, an indication that the one or more corresponding parameters were selected; determining, responsive to receiving the indication, an equivalent one of the one or more predetermined parameters for each of the selected one or more corresponding parameters; and presenting the equivalent parameters as replacement parameters, wherein the instruction to select one or more predetermined parameters comprises a confirmation that the one or more predetermined parameters are most equivalent parameters to the one or more corresponding parameters.

Clause 20. The non-transitory machine-readable storage medium of Clause 16, wherein the operations further comprise: receiving, at a server, a first indication of a medical device and a second indication of the existing drug library software package for operation on the medical device; determining, based on receiving the first indication and the second indication, that the medical device is of the target medical device type, and that the existing drug library software package is associated with the existing medical device type and incompatible with the target medical device type; and responsive to determining that the existing drug library software package is associated with the existing medical device type and the medical device is of the target medical device type, performing the identifying, analyzing steps, and providing steps.

Further Consideration:

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals.

Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device, diagnostic device, monitoring device, or server in communication therewith.

What is claimed is:

1. A method for migrating an existing drug library software package to a new medical device in order to configure the new medical device, comprising:

identifying an existing drug library software package configured in an existing library format corresponding to an existing medical device type, the existing drug library software package including one or more drug entries, a drug entry being associated with a set of operating parameters or configuration information for configuring a programmable medical device of the existing medical device type when loaded into a memory of the programmable medical device;

automatically analyzing the existing drug library software package to determine first drug library information compatible with a target library format corresponding to a target medical device type, and to identify second drug library information not within the first compatible drug library information and which is not compatible with the target library format, wherein the second drug library information not being compatible with the target library format includes the second drug library information causing an error response from a respective device of the target medical device type if loaded by the respective device;

providing for display, based on the analyzing, a user interface that presents at least a portion of the determined first drug library information and identifies one or more incompatible parameters from the second drug library information identified as not being compatible with the target library format;

receiving, via the user interface, a selection of the one or more incompatible parameters selected from the second drug library information identified as not being compatible with the target library format and a selection of one or more predetermined parameters in the target library format to replace the one or more incompatible parameters and for inclusion in a new drug library software package configured in the target library format and which includes the determined first drug library information and the selected one or more predetermined parameters;

receiving an indication via the user interface to generate the new drug library software package; and responsive to receiving the indication:

generating the new drug library software package in the target library format based on the compatible first drug library information and the selected one or more predetermined parameters; and providing the new drug library software package for downloading to a memory of a medical device of the target medical device type, wherein the medical device is configured to utilize parameter configurations of the new drug library software package when the new drug library software package is downloaded to the memory.

2. The method of claim 1, further comprising:

receiving, at a server, a request to generate the new drug library software package for a medical device, and a selection of the existing drug library software package, wherein the existing drug library software package is identified in a database by the server responsive to receiving the request and selection, and wherein the analyzing, providing of the user interface, receiving, and generating are performed by the server.

3. The method of claim 2, further comprising:

providing the new drug library software package to the medical device of the target medical device type.

4. The method of claim 1, further comprising:

receiving, via the user interface, an indication that the one or more incompatible parameters were selected;

determining, responsive to receiving the indication, an equivalent one of the one or more predetermined parameters for each of the selected one or more incompatible parameters; and presenting the equivalent parameters as replacement parameters, wherein the user interface comprises a confirmation that the one or more predetermined parameters are equivalent parameters to the one or more incompatible parameters.

5. The method of claim 4, wherein determining the equivalent one of the one or more predetermined parameters comprises:

determining, for a first parameter of the one or more incompatible parameters, that the first parameter is within a range of values corresponding to a respective parameter of the predetermined parameters.

6. The method of claim 1, receiving, via the user interface, an instruction to delete a parameter of the second drug library information identified as not being within the compatible first drug library information.

7. The method of claim 1, further comprising:

receiving, at a server, from a medical device a first indication of the medical device and a second indication of the existing drug library software package for operation on the medical device;

determining, based on receiving the first indication and the second indication, that the medical device is of the target medical device type, and that the existing drug library software package is associated with the existing medical device type and incompatible with the target medical device type; and responsive to determining that the existing drug library software package is associated with the existing medical device type and the medical device is of the target medical device type, performing the identifying, analyzing steps, and providing steps.

8. A system for migrating an existing drug library software package to a new medical device in order to configure the new medical device, comprising:

one or more processors; and memory including instructions that, when executed by the one or more processors, cause the one or more processors to:

identify an existing drug library software package configured in an existing library format corresponding to an existing medical device type, the existing drug library software package including one or more drug entries, a drug entry being associated with a set of operating parameters or configuration information for configuring a programmable medical device of the existing medical device type when loaded into a memory of the programmable medical device;

automatically analyze the existing drug library software package to determine first drug library information compatible with a target library format corresponding to a target medical device type, and to identify second drug library information not within the first drug library information and which is not compatible with the target library format, wherein the second drug library information not being compatible with the target library format includes the second drug library information causing an error response from a respective device of the target medical device type if loaded by the respective device;

provide for display, based on the analyzing, a user interface that presents at least a portion of the determined first drug library information and identifies one or more incompatible parameters from the second drug library information identified as not being compatible with the target library format;

receive, via the user interface, a selection of the one or more incompatible parameters selected from the second drug library information identified as not being compatible with the target library format and a selection of one or more predetermined parameters in the target library format to replace the one or more incompatible parameters and for inclusion in a new drug library software package configured in the target library format and which includes the determined first drug library information and the selected one or more predetermined parameters;

receive an indication via the user interface to generate the new drug library software package; and responsive to receiving the indication:

generate the new drug library software package in the target library format based on the first compatible drug library information and the selected one or more predetermined parameters; and provide the new drug library software package for downloading to a memory of a medical device of the target medical device type, wherein the medical device is configured to utilize parameter configurations of the new drug library software package when the new drug library software package is downloaded to the memory.

9. The system of claim 8, wherein the instructions, when executed, further cause the one or more processors to:

receive, at a server, a request to generate the new drug library software package for a medical device of the target medical device type, and a selection of the existing drug library software package, wherein the existing drug library software package is identified in a database by the server responsive to receiving the request and selection, and wherein the analyzing, providing of the user interface, receiving, and generating are performed over a network.

10. The system of claim 9, wherein the instructions, when executed, further cause the one or more processors to:

provide the new drug library software package to the medical device of the target medical device type.

11. The system of claim 8, wherein the instructions, when executed, further cause the one or more processors to:

receive, via the user interface, an indication that the one or more incompatible parameters were selected;

determine, responsive to receiving the indication, an equivalent one of the one or more predetermined parameters for each of the selected one or more incompatible parameters; and provide the equivalent parameters as replacement parameters, wherein the instruction to select one or more predetermined parameters comprises a confirmation that the one or more predetermined parameters are equivalent parameters to the one or more incompatible parameters.

12. The system of claim 11, wherein determining the equivalent one of the one or more predetermined parameters comprises:

causing the one or more processors to determine, for a first parameter of the selected one or more incompatible parameters, that the first parameter is within a range of values corresponding to a respective parameter of the predetermined parameters.

13. The system of claim 8, wherein the instructions, when executed, further cause the one or more processors to:

receive, via the user interface, an instruction to delete a parameter of the second drug library information identified as not being within the first compatible drug library information.

14. The system of claim 8, wherein the instructions, when executed, further cause the one or more processors to:

receiving, at a server, a first indication of a medical device and a second indication of the existing drug library software package for operation on the medical device;

determining, based on receiving the first indication and the second indication, that the medical device is of the target medical device type, and that the existing drug library software package is associated with the existing medical device type and incompatible with the target medical device type; and responsive to determining that the existing drug library software package is associated with the existing medical device type and the medical device is of the target medical device type, performing the identifying, analyzing steps, and providing steps.

15. The system of claim 14, wherein the user interface is provided for display at the medical device.

16. A non-transitory machine-readable storage medium embodying instructions that, when executed by a machine, cause the machine to perform operations for migrating an existing drug library software package to a new medical device in order to configure the new medical device, comprising:

identifying an existing drug library software package configured in an existing library format corresponding to an existing medical device type, the existing drug library software package including one or more drug entries, a drug entry being associated with a set of operating parameters or configuration information for configuring a programmable medical device of the existing medical device type when loaded into a memory of the programmable medical device;

automatically analyzing the existing drug library software package to determine first drug library information compatible with a target library format corresponding to a target medical device type, and to identify second drug library information not within the first drug library information and which is not compatible with the target library format, wherein the second drug library information not being compatible with the target library format includes the second drug library information causing an error response from a respective device of the target medical device type if loaded by the respective device;

providing for display, based on the analyzing, a user interface that presents at least a portion of the determined first drug library information and identifies one or more incompatible parameters from the second drug library information identified as not being compatible with the target library format;

receiving, via the user interface, a selection of the one or more incompatible parameters selected from the second drug library information identified as not being compatible with the target library format and a selection of one or more predetermined parameters in the target library format to replace the one or more incompatible parameters and for inclusion in a new drug library software package configured in the target library format and which includes the determined first drug library information and the selected one or more predetermined parameters;

receiving an indication via the user interface to generate the new drug library software package; and responsive to receiving the indication:

generating the new drug library software package in the target library format based on the compatible first drug library information and the selected one or more predetermined parameters; and providing the new drug library software package for downloading to a memory of a medical device of the target medical device type, wherein the medical device is configured to utilize parameter configurations of the new drug library software package when the new drug library software package is downloaded to the memory.

17. The non-transitory machine-readable storage medium of claim 16, wherein the operations further comprise:

receiving, at a server, a request to generate the new drug library software package for a medical device of a new second medical device type, and a selection of the existing drug library software package, wherein the existing drug library software package is identified in a database by the server responsive to receiving the request and selection, and wherein the analyzing, providing of the user interface, receiving, and generating are performed by the server.

18. The non-transitory machine-readable storage medium of claim 17, wherein the operations further comprise:

providing the new drug library software package to the medical device of the new second medical device type.

19. The non-transitory machine-readable storage medium of claim 16, further comprising:

receiving, via the user interface, an indication that the one or more incompatible parameters were selected;

determining, responsive to receiving the indication, an equivalent one of the one or more predetermined parameters for each of the selected one or more incompatible parameters; and presenting the equivalent parameters as replacement parameters, wherein the selection of the one or more predetermined parameters comprises a confirmation that the one or more predetermined parameters are equivalent parameters to the one or more incompatible parameters.

20. The non-transitory machine-readable storage medium of claim 16, wherein the operations further comprise:

receiving, at a server, a first indication of a medical device and a second indication of the existing drug library software package for operation on the medical device;

determining, based on receiving the first indication and the second indication, that the medical device is of the target medical device type, and that the existing drug library software package is associated with the existing medical device type and incompatible with the target medical device type; and responsive to determining that the existing drug library software package is associated with the existing medical device type and the medical device is of the target medical device type, performing the identifying, analyzing steps, and providing steps.

*    *    *    *    *